United States Patent
Kamikoriyama et al.

(10) Patent No.: US 10,994,331 B2
(45) Date of Patent: May 4, 2021

(54) COPPER POWDER AND CONDUCTIVE COMPOSITION CONTAINING SAME

(71) Applicant: Mitsui Mining & Smelting Co., Ltd., Tokyo (JP)

(72) Inventors: Yoichi Kamikoriyama, Saitama (JP); Mami Yoshida, Saitama (JP); Hiroshi Imamura, Saitama (JP); Yuji Asano, Saitama (JP)

(73) Assignee: MITSUI MINING & SMELTING CO., LTD., Tokyo (JP)

( * ) Notice: Subject to any disclaimer, the term of this patent is extended or adjusted under 35 U.S.C. 154(b) by 67 days.

(21) Appl. No.: 15/554,269

(22) PCT Filed: Jan. 19, 2016

(86) PCT No.: PCT/JP2016/051462
§ 371 (c)(1),
(2) Date: Aug. 29, 2017

(87) PCT Pub. No.: WO2016/152214
PCT Pub. Date: Sep. 29, 2016

(65) Prior Publication Data
US 2018/0079001 A1    Mar. 22, 2018

(30) Foreign Application Priority Data
Mar. 26, 2015 (JP) .............................. JP2015-065181

(51) Int. Cl.
*B22F 1/00* (2006.01)
*B22F 1/02* (2006.01)
(Continued)

(52) U.S. Cl.
CPC .............. *B22F 1/0062* (2013.01); *B22F 1/00* (2013.01); *B22F 1/0044* (2013.01);
(Continued)

(58) Field of Classification Search
None
See application file for complete search history.

(56) References Cited

U.S. PATENT DOCUMENTS

| | | | | |
|---|---|---|---|---|
| 4,663,079 A | * | 5/1987 | Yamaguchi | .......... C08K 5/3472 174/102 SC |
| 4,921,623 A | * | 5/1990 | Yamaguchi | .............. C09D 5/24 252/500 |

(Continued)

FOREIGN PATENT DOCUMENTS

| | | |
|---|---|---|
| JP | S61-54033 A | 3/1986 |
| JP | 2010-065315 | 3/2010 |

(Continued)

OTHER PUBLICATIONS

Translation of JP 2014-186952 (originally published Oct. 2, 2014) from Espacenet.*

(Continued)

*Primary Examiner* — George Wyszomierski
(74) *Attorney, Agent, or Firm* — Nixon & Vanderhye (57) ABSTRACT

There is provided a copper powder containing an organic compound containing carbon and nitrogen. The powder has a ratio of carbon content PC (mass %) to specific surface area SSA (m²/g), PC/SSA, of 0.005 to 0.1 and a ratio of nitrogen content PN (mass %) to specific surface area SSA (m²/g), PN/SSA, of 0.001 to 0.05. The organic compound preferably contains two or more of nitrogen atom per molecule and is preferably capable of forming a five-membered ring complex with copper. The organic compound preferably includes one or more of dimethyl glyoxime, ethylenediamine, and polyethyleneimine.

6 Claims, 4 Drawing Sheets (51) Int. Cl.
- H01B 5/00 (2006.01)
- H01B 1/22 (2006.01)
- H01B 1/02 (2006.01)
- C07C 211/09 (2006.01)
- C07C 251/58 (2006.01)
- C08G 73/02 (2006.01)

(52) U.S. Cl.
CPC .............. *B22F 1/0074* (2013.01); *B22F 1/02* (2013.01); *H01B 1/026* (2013.01); *H01B 1/22* (2013.01); *H01B 5/00* (2013.01); *C07C 211/09* (2013.01); *C07C 251/58* (2013.01); *C08G 73/02* (2013.01)

(56) References Cited

U.S. PATENT DOCUMENTS

| | | | | |
|---|---|---|---|---|
| 5,779,941 | A * | 7/1998 | Umeda | C07C 251/04 252/512 |
| 9,846,362 | B2 | 12/2017 | Mizuguchi et al. | |
| 2009/0261304 | A1* | 10/2009 | Mori | B22F 1/0022 252/512 |
| 2010/0230644 | A1* | 9/2010 | Ryoshi | B22F 1/0022 252/512 |
| 2014/0203222 | A1 | 7/2014 | Ito et al. | |
| 2015/0266090 | A1 | 9/2015 | Kamikoriyama et al. | |
| 2015/0370167 | A1 | 12/2015 | Mizuguchi et al. | |
| 2018/0169755 | A1* | 6/2018 | Tagami | B22F 1/00 |

FOREIGN PATENT DOCUMENTS

| | | |
|---|---|---|
| JP | 2014-186952 | 10/2017 |
| KR | 10-2009-0105843 | 10/2009 |
| WO | 2012-067016 | 5/2012 |
| WO | WO 2012/157704 | 11/2012 |
| WO | 2014-080662 | 5/2014 |
| WO | 2014-156677 | 10/2014 |

OTHER PUBLICATIONS

International Search Report, PCT/JP2016/051462, dated Apr. 5, 2016.
Extended European Search Report for Application No. 16768117 dated Oct. 12, 2018.
Notice of Reasons for Refusal for Japanese Patent Application No. 2017-507536 dated Aug. 18, 2020.

* cited by examiner

COPPER POWDER AND CONDUCTIVE COMPOSITION CONTAINING SAME

TECHNICAL FIELD

This invention relates to copper powder and an electroconductive composition containing the same.

BACKGROUND ART

Copper is widely used on an industrial scale as a conductive material for its high electrical conductivity and inexpensiveness. However, because copper is susceptible to oxidation, it easily reduces in conductivity. Reduction of conductivity is remarkable in the case when copper is in the form of powder with a large specific surface area. Hence, with a view to preventing reduction of conductivity, copper powder for use as a conductive material is frequently surface-treated for oxidation resistance enhancement. Various organic compounds, for example, are used for the surface treatment.

Patent Literature 1 below discloses an organic compound having a hydrophobic group and a chelating group per molecule as an example of the organic compounds used for the surface treatment. The hydrophobic group is exemplified by a long chain alkyl group and a cyclic alkyl group, and the chelating group is exemplified by aminocarboxylic acids, such as ethylenediaminediacetic acid and ethylenediaminetetraacetic acid. Patent Literature 2 below teaches attaching to copper particles benzotriazole or a derivative thereof, an organic amine, a fatty acid, a metal alkoxide, or the like by physical or chemical adsorption.

CITATION LIST

Patent Literature

Patent Literature 1: JP 2010-65315A
Patent Literature 2: WO 2012/157704

SUMMARY OF INVENTION

Copper powder can be made into a paste, and the paste is spread on a substrate to form a coating film, which is then fired to form a conductor. On firing, a carbonaceous component of the paste is oxidized or decomposed, and released in the form of decomposition gas. The released decomposition gas negatively affects the denseness of the conductor, which can result in an increase in electrical resistance. The organic compound used for the copper powder surface treatment can remain after firing, which will cause an increase in electrical resistance of the conductor.

Copper-containing paste is not only used as a conductive material but often used as a substitute for solder. In recent years there has been increasing use of a semiconductor device called a power device as power conversion and control equipment, such as an inverter. Because power devices are for controlling a high current unlike integrated circuits such as memories and microprocessors, they generate a very large amount of heat in operation. Accordingly, heat resistance is required of the solder used to mount a power device. Lead-free solder, which is currently widespread, has a disadvantage of low heat resistance. Then, various techniques replacing the use of solder have been proposed, in which metallic particles are applied to a substrate through various coating means to form a sintered film. Paste compositions that have so far been proposed as a joint material substituting for solder have higher heat resistance than solder but still leave room for improvement on joint strength to the substrate. In addition, a solder joint can remelt when exposed to high temperatures.

An object of the invention is to provide an improvement in copper powder suited for use as a conductor or a joint material, more particularly, to provide a copper powder having improved oxidation resistance and yet having reduced tendency to gas evolution on firing and a conductive composition containing the copper powder.

The present invention provides a copper powder containing a carbon- and nitrogen-containing organic compound, having a ratio of carbon content PC (mass %) to specific surface area SSA ($m^2/g$), PC/SSA, of 0.005 to 0.1, and a ratio of nitrogen content PN (mass %) to specific surface area SSA ($m^2/g$), PN/SSA, of 0.001 to 0.05.

The present invention also provides an electroconductive composition comprising the copper powder described above and an organic solvent.

DESCRIPTION OF EMBODIMENTS

The present invention will be described on the basis of its preferred embodiments. The copper powder of the invention is an aggregate of copper particles. The copper particles herein encompass particles made of pure copper and particles made of a copper base alloy. The term "copper base alloy" means an alloy containing at least 50 mol % of copper and examples thereof includes a copper-nickel alloy, a copper-zinc alloy, and a copper-tin alloy. As used herein, the term "copper powder" means, depending on context, an aggregate of copper particles or individual copper particles.

Elemental analysis will detect carbon and nitrogen in the copper powder of the invention. In other words, the copper powder of the invention contains carbon and nitrogen, which are derived from the organic compound used for the surface treatment of copper particles. As used herein, the term "surface treatment" covers treatments in general for the formation of a coating film on the surface of a copper particle to break contact with oxygen thereby to protect copper from oxidation, including what is called an antioxidation treatment, an anticorrosion treatment, and so on.

Generally speaking, the organic compound used for the surface treatment exhibits higher oxidation inhibitory effect with an increase in the amount of the organic compound covering the surface of the copper particle. An increase in the amount of coating, on the other hand, can be a cause of increase in electrical resistance of a conductor. The inventors have conducted extensive investigations searching for a means for controlling an increase in electrical resistance while inhibiting oxidation of copper. As a result, they have found it extremely effective to attach a specific amount of an organic compound containing carbon and nitrogen onto the surface of copper powder and completed the invention. In the following description, the copper powder having been surface treated with the organic compound will be referred to as surface-treated copper powder for the sake of convenience.

The shape and surface condition of copper powder particles vary according to the process of production, and therefore so does the specific surface area. Therefore, it is practical to define the amount of the organic compound attached to the surface of copper powder on the basis of the specific surface area of copper powder. The inventors have studied on the amount of the attached organic compound from that viewpoint and, as a result, it has been found advantageous with a view to inhibiting copper oxidation while preventing increase of electrical resistance of a conductor that a ratio of the carbon content PC (mass %) of copper powder to the specific surface area SSA ($m^2/g$) of copper powder. PC/SSA, be in the range of from 0.005 to 0.1, preferably 0.005 to 0.09, more preferably 0.010 to 0.08, even more preferably 0.010 to 0.07. With the same view, it is preferred that the ratio of the nitrogen content PN (mass %) of copper powder to SSA, PN/SSA, be in the range of from 0.001 to 0.05, preferably 0.001 to 0.045, more preferably 0.002 to 0.045, even more preferably 0.002 to 0.040.

The methods for determining the SSA, PC, and PN will be described in Examples given later. As used herein, the term "specific surface area (SSA)" is intended to refer to the specific surface area of either copper powder with no organic compound attached thereto or copper powder with an organic compound attached thereto. Whether or not the copper powder has an organic compound attached thereto makes substantially no difference in the results of determination of specific surface area because the amount of the organic compound attached to the copper powder is very small.

Although Patent Literature 2 cited above also teaches about limiting the PC/SSA value to within a specific range, it is not considered in the document that limiting not only the PC/SSA but PN/SSA to within the respective specific ranges may enable preventing copper oxidation while controlling increase in electrical resistance of a conductor. In addition, the document states that there is no lower limit on the PC/SSA value. That is, the technique of Patent Literature 2 includes an embodiment in which the copper powder has a zero carbon content, i.e., the copper powder is not surface treated with an organic compound and is, therefore, clearly different from the present invention, in which the use of an organic compound is essential to carry out the surface treatment.

The organic compound suitably used in the invention contains carbon and nitrogen as discussed above, is able to protect copper atoms from contact with oxygen in a small amount, and has reduced tendency to gas evolution on firing in any of an oxygen-containing atmosphere, an inert atmosphere, and a reducing atmosphere. It is preferred to use an organic compound containing carbon and nitrogen in the molecule and capable of forming a complex with copper. Such an organic compound shows high strength of chemically bonding to copper and therefore exhibits high ability to protect copper atoms from oxygen even in a small amount. From this standpoint, it is advantageous to use an organic compound having a carbon skeleton structure in the molecule, containing at least one nitrogen atom bonded to the carbon skeleton structure, and being capable of forming a complex with copper via the nitrogen atom. It is particularly preferred to treat the copper powder surface using an organic compound containing two or more of nitrogen atom per molecule and capable of forming a five-membered ring complex with copper.

Examples of the organic compound that is suitably used for the surface treatment in the invention include ethylenediamine, polyethyleneimine, and dimethyl glyoxime. These compounds may be used either individually or in combination of two or more thereof. In the case of using polyethyleneimine, the polyethyleneimine preferably has a number average molecular weight of 100 to 100,000, more preferably 300 to 70,000, as determined by the ebullioscopic method or the viscosity method.

Ethylenediamine, polyethyleneimine, and dimethyl glyoxime, which are enumerated above as illustrative examples of the organic compound, are especially preferred in view of their containing two or more of nitrogen atom per molecule and capability of forming a five-membered ring complex with copper to exhibit high chemical bond strength to copper thereby to have high ability to block oxygen from copper atom even in a small amount. In addition, seeing that these organic compounds produce sufficient effect even in a small amount, the amount of decomposition gas generated on firing is advantageously reduced in any of an oxygen-containing atmosphere, an inert atmosphere, and a reducing atmosphere.

The amount of the organic compound present in the copper powder of the invention is very small. Specifically, when the content of the organic compound in the copper powder is expressed in terms of the carbon content PC, the PC is preferably 0.005 to 1 mass %, more preferably 0.005 to 0.5 mass %, even more preferably 0.01 to 0.3 mass %. When the content is expressed in terms of the nitrogen content PN, the PN is preferably 0.001 to 0.5 mass %, more preferably 0.01 to 0.3 mass %, even more preferably 0.01 to 0.1 mass %.

In the invention, the amount of the organic compound to be used for the surface treatment is represented in terms of the contents of carbon and nitrogen composing the organic compound, and the quotients of the carbon and nitrogen contents divided by the specific surface area of the copper powder are specified. Therefore, the invention is applicable to a wide range of copper powders from fine particles to relatively coarse particles. While the average primary particle size D of copper particles composing the copper powder of the invention is not particularly critical, there naturally is a lower limit to the industrially practical particle size, considering that particles with a smaller particle size are more susceptible to oxidation. On the other hand, a suitable upper limit is set on the particle size, considering that the invention is suited for application to small-diameter copper particles that are susceptible to the influence of oxidation. Specifically, the average primary particle size D is preferably 10 nm to 10 μm, more preferably 20 nm to 5 μm, even more preferably 50 nm to 3 μm. The invention offers the advantage that oxidation of copper powder is retarded irrespective of the primary particle size of the copper powder. As used herein, the term "primary particle" refers to an electron-microscopically recognizable smallest unit of an aggregate of copper atoms, which can be a multicrystal or a single crystal. The method for determining the average primary particle size D will be described in Examples given later. As used herein, the term "average primary particle size D" is intended to refer to the particle size of either copper powder with no organic compound attached thereto or copper powder with an organic compound attached thereto. Whether or not the copper powder has an organic compound attached thereto makes substantially no difference in the results of determination of average primary particle size D because the amount of the organic compound attached to the copper powder in the invention is very small.

Having been surface-treated for oxidation resistance enhancement with a small amount of the organic compound as stated, the copper powder of the invention evolves a reduced amount of decomposition gas on being heated. Specifically, with the amount of evolved decomposition gas being expressed in terms of the weight loss of the copper powder when heated in a nitrogen atmosphere from 25° C. up to 500° C. in thermogravimetry, the weight loss of the copper powder of the invention is preferably as small as 0.8 mass % or less, more preferably 0.7 mass % or less, even more preferably 0.6 mass % or less. Therefore, a conductor formed by firing using the copper powder of the invention is less likely to have defects such as cracks and voids. Understandably there is no lower limit to the weight loss. The smaller the weight loss, the more preferred.

The shape of the copper particles composing the copper powder of the invention are not particularly limited. The copper particles may have various shapes according to the process of production, and copper particles of any shape appropriate to the intended use may be chosen. For example, copper particles may be spherical, polyhedral, or flattened. The copper powder of the invention may be composed of copper particles of any one or a combination of two or more of these shapes.

The process for producing copper particles to be surface-treated is not particularly limited, and any process so far known in the art can be used as appropriate. For example, a wet reduction process using a reducing agent or an atomization process may be used. Commercially available copper powder products are also usable.

The surface treatment of the thus provided copper particles with an organic compound is carried out by, for example, mixing a slurry of the copper particles with the organic compound and removing the liquid component from the mixture by filtration, drying, or a like means to leave the organic compound on the surface of the copper particles. It is noted that the inventors have confirmed that substantially no effect of the organic compound on oxidation resistance is developed if the organic compound is added to any system in the course of copper particles synthesis.

The thus surface-treated copper powder of the invention may be dispersed in a medium, such as water or an organic solvent, to make a slurry for actual use. The copper powder of the invention may be dried for use in the form of dry powder. The copper powder of the invention may be mixed with an organic solvent, a resin, and the like to provide a conductive composition, such as a conductive ink or a conductive paste, as will be described below.

The conductive composition containing the copper powder of the invention is composed of at least the copper powder and an organic solvent. The organic solvent may be any of those conventionally used in the field of metal powder-containing conductive compositions. Illustrative examples of such organic solvents include alcohols, polyhydric alcohols, polyhydric alcohol alkyl ethers, polyhydric alcohol aryl ethers, esters, nitrogen-containing heterocyclic compounds, amides, amines, and saturated hydrocarbons. These organic solvents can be used either individually or in combination of two or more thereof.

Examples of the alcohols include 1-propanol, 1-butanol, 1-pentanol, 1-hexanol, cyclohexanol, 1-heptanol, 1-octanol, 1-nonanol, 1-decanol, glycidol, benzyl alcohol, methylcyclohexanol, 2-methyl-1-butanol, 3-methyl-2-butanol, 4-methyl-2-pentanol, isopropyl alcohol, 2-ethylbutanol, 2-ethylhexanol, 2-octanol, 2-methoxyethanol, 2-ethoxyethanol, 2-n-butoxyethanol, and 2-phenoxyethanol.

Examples of the polyhydric alcohols include ethylene glycol, propylene glycol, 1,3-propanediol, 1,4-butanediol, 1,5-pentanediol, diethylene glycol, dipropylene glycol, triethylene glycol, and tetraethylene glycol.

Examples of the polyhydric alcohol alkyl ethers include ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, triethylene glycol monomethyl ether, triethylene glycol monoethyl ether, and propylene glycol monobutyl ether.

Examples of the polyhydric alcohol aryl ethers include ethylene glycol monophenyl ether. Examples of the esters include ethyl cellosolve acetate, butyl cellosolve acetate, and γ-butyrolactone. Examples of the nitrogen-containing heterocyclic compounds include N-methylpyrrolidone and 1,3-dimethyl-2-imidazolidinone. Examples of the amides include formamide, N-methylformamide, and N,N-dimethylformamide. Examples of the amines include monoethanolamine, diethanolamine, triethanolamine, tripropylamine, and tributylamine.

Examples of the saturated hydrocarbons include heptane, octane, nonane, decane, undecane, dodecane, tridecane, tetradecane, pentadecane, and hexadecane.

Where needed, the conductive composition of the invention may contain a dispersant. The dispersant is preferably a nonionic surfactant free from sodium, calcium, phosphorus, sulfur, and chlorine. Examples of such nonionic surfactants include polyhydric alcohol fatty acid esters, propylene glycol fatty acid esters, glycerol fatty acid esters, polyglycerol fatty acid esters, polyoxyethylene glycerol fatty acid esters, polyoxyethylene alkyl ethers, polyoxyethylene polyoxypropylene alkyl ethers, polyoxyalkylene alkyl ethers, sorbitan fatty acid esters, polyoxyethylene sorbitan fatty acid esters, polyoxyethylene sorbitol fatty acid esters, polyoxyethylene hydrogenated castor oil, polyoxyethylene alkylamines, polyoxyalkylene alkylamines, alkylalkanolamides, and polyoxyethylene alkyl phenyl ethers.

The conductive composition of the invention may further contain an organic vehicle or a glass frit. The organic vehicle contains a resin component and a solvent. Examples of the resin component are acrylic resins, epoxy resins, ethyl cellulose, and carboxyethyl cellulose. Examples of the solvent include terpene solvents, such as terpineol and dihydroterpineol, and ether solvents, such as ethyl carbitol and butyl carbitol. Examples of the glass frit include borosilicate glass, barium borosilicate glass, and zinc borosilicate glass.

If desired, the conductive composition of the invention may further contain copper powder other than the copper powder of the invention in order to improve various performance properties of the conductive composition.

The compounding ratios of the copper powder and the organic solvent may be adjusted in a broad range according to the intended use of the conductive composition or the method of applying the conductive composition. Suitable methods of application include inkjet printing, dispenser printing, microdispenser printing, gravure printing, screen printing, dip coating, spin coating, spray coating, bar coating, and roller coating.

The viscosity of the conductive composition of the invention may vary depending on the copper powder content, and the conductive composition is called ink, slurry, paste, and so on according to the viscosity. The copper powder content of the conductive composition of the invention may widely range from 5 to 95 mass %, for example. When an inkjet printing is selected as a coating technique, the copper powder content of the composition is preferably 10 to 50 mass %, for example. The copper powder content suitable for dispenser printing is preferably 40 to 90 mass %, for example. The copper powder content suited for screen printing is preferably 89 to 94 mass %, for example.

The conductive composition of the invention may be applied to a substrate to form a coating film, which is then fired to form a conductor. The conductor is suitable to provide circuits of printed wiring boards or to secure electrical connection for an external electrode of a ceramic capacitor. The substrate to be used is selected, according to the type of electronic circuits using the copper powder, from wiring boards made of glass epoxy resins and flexible wiring boards made of polyimides, and the like.

The coating film formed on the substrate may be fired at any temperature above the sintering onset temperature. The temperature of firing the coating film is preferably 140° C. to 350° C., more preferably 150° C. to 325° C., even more preferably 170° C. to 300° C. The firing is preferably carried out in a non-oxidizing atmosphere. The conductive composition of the invention is effectively prevented from having an increased electrical resistance as a conductor that is ascribed to generation of a large quantity of decomposition gas when fired in an inert atmosphere or a reducing atmosphere.

The thus formed conductor has increased conductivity owing to the copper powder of the invention that is used as a constituent component of the conductive composition. The conductive composition of the invention is thus suited to form, for example, a crack- and/or void-free conductor in reflow firing.

Since the amount of the organic compound used for the copper powder surface treatment is held down as stated, the sintered body formed by using the copper powder of the invention is advantageous in that, when used as a substitute for solder, it starts to sinter at low temperatures and gains an increased joint strength. For example, the composition containing the copper powder of the invention can be disposed between two objects to be joined and sintered by heating to form a copper sintered body, by which the two objects are joined together. The thus formed sintered body (joint material) joins the two objects with high joint strength. In addition, the sintered body exhibits high electrical conductivity. Therefore, the sintered body is also usable as a conductive material. For example, the composition containing the copper powder of the invention can be used as a conductive joint material in mounting surface mount electronic devices on a printed wiring board. The composition is preferably in the form of paste containing not only the copper powder of the invention but a liquid medium selected from a variety of organic solvents described supra. The composition may contain copper powder other than the copper powder of the invention unless the effect as a joint material is impaired.

In the step of firing, the temperature of heating the composition containing the copper powder of the invention is preferably 140° C. to 350° C., more preferably 150° C. to 325° C., even more preferably 170° C. to 300° C., while varying depending on the materials of the objects to be joined. When fired at temperatures within the above range, the composition provides a sintered body with sufficiently enhanced joint strength and sufficiently increased conductivity.

In order to ensure the further improvements on the joint strength and conductivity of the resulting sintered body, it is advantageous that the firing to sinter the composition containing the copper powder of the invention be carried out in a non-oxidizing atmosphere. Examples of the non-oxidizing atmosphere include an inert atmosphere (e.g., a nitrogen atmosphere) and a reducing atmosphere (e.g., formic acid atmosphere and hydrogen atmosphere). A formic acid, a hydrogen, or a like non-oxidizing atmosphere is preferred in the interests of further improvements on joint strength and conductivity. A nitrogen or a like inert atmosphere is advantageous from the industrial viewpoint, such as economy and safety.

The joint formed of the sintered body preferably has a joint strength of 10 MPa or greater, more preferably 20 MPa or greater, even more preferably 30 MPa or greater. The higher, the better. Therefore there is no critical upper limit on the joint strength, but the upper limit would be about 100 MPa in the light of the inventors' experience. As used herein, the term "joint strength" is defined to be shear strength. The method for determining the joint strength will be described in Examples hereinafter given.

Power devices taking advantage of the high temperature characteristics of wide-band-gap semiconductors, such as SiC, are expected to become more and more efficient, smaller and smaller, and lighter and lighter and to make a contribution to increasing the efficiency of every next-generation power source of, e.g., electric cars and industrial power-driven equipment. The composition containing the copper powder of the invention contributes largely to widely spreading these next-generation power devices over the whole society.

EXAMPLES

The invention will now be illustrated in greater detail with reference to Examples, but it should be understood that the invention is not deemed to be limited thereto. Unless otherwise noted, all the percentages are by mass.

Example 1

In a 5-liter beaker were put 510 g of copper acetate, 1000 g of pure water, and 780 g of 2-propanol and stirred at room temperature. To the mixture was added 60 g of hydrazine monohydrate. After stirring for 30 minutes, an additional 570 g hydrazine monohydrate was added, followed by stirring at 60° C. for 2 hours to synthesize copper powder. After cooling, the copper powder was precipitated and repulped with water until the conductivity of the washing reduced to 10 mS/cm or less. The average primary particle size D (Heywood diameter) of the resulting copper powder was 180 nm as determined by the method described below. The resulting washed slurry was heated up to 50° C. and stirred, and 0.8 g of dimethyl glyoxime dissolved in 200 ml of methanol was added thereto, followed by stirring for 1 hour to attach dimethyl glyoxime to the surface of the copper powder. The thus treated copper powder was collected by filtration and dried in vacuo to give 130 g of a dimethyl glyoxime-treated copper powder.

Example 2

Copper powder was synthesized and washed in the same manner as in Example 1. The resulting washed slurry was heated to 50° C. and stirred. To the slurry was added 1.6 g of ethylenediamine dissolved in 200 ml of methanol, followed by stirring for 1 hour to attach ethylenediamine to the surface of the copper powder. The thus treated copper powder was collected by filtration and dried in vacuo to give 110 g of an ethylenediamine-treated copper powder.

Example 3

Copper powder was synthesized and washed in the same manner as in Example 1. The resulting washed slurry was heated to 50° C. and stirred. To the slurry was added 1.6 g of polyethyleneimine (molecular weight: 1800) dissolved in 200 ml of methanol, followed by stirring for 1 hour to attach polyethyleneimine to the surface of the copper powder. The thus treated copper powder was collected by filtration and dried in vacuo to give 132 g of a polyethyleneimine-treated copper powder.

Example 4

The same procedures as in Example 1 were repeated, except for changing the amount of dimethyl glyoxime to 2.4 g to obtain 127 g of a dimethyl glyoxime-treated copper powder.

Comparative Example 1

Copper powder was synthesized and washed in the same manner as in Example 1. The resulting washed slurry was heated to 50° C. and stirred. To the slurry was added 1.6 g of lauric acid dissolved in 200 ml of methanol, followed by stirring for 1 hour to attach lauric acid to the surface of the copper powder. The thus treated copper powder was collected by filtration and dried in vacuo to give 133 g of a lauric acid-treated copper powder.

Comparative Example 2

Copper powder was synthesized and washed in the same manner as in Example 1. The resulting washed slurry was heated to 50° C. and stirred. To the slurry was added 1.6 g of benzotriazole dissolved in 200 ml of methanol, followed by stirring for 1 hour to attach benzotriazole to the surface of the copper powder. The thus treated copper powder was collected by filtration and dried in vacuo to give 140 g of a benzotriazole-treated copper powder.

Example 5

A dimethyl glyoxime-treated copper powder was prepared in the same manner as in Example 1, except for using CS-10, a copper powder available from Mitsui Mining & Smelting Co., Ltd., as copper powder to be surface treated. CS-10 had an average primary particle size D of 0.82 μm.

Comparative Example 3

A stearylamine-treated copper powder was prepared in the same manner as in Example 1, except for using CS-10, a copper powder available from Mitsui Mining & Smelting Co., Ltd., as copper powder to be surface treated and using stearylamine as an organic compound. CS-10 had an average primary particle size D of 0.80 μm.

Figure 1A:
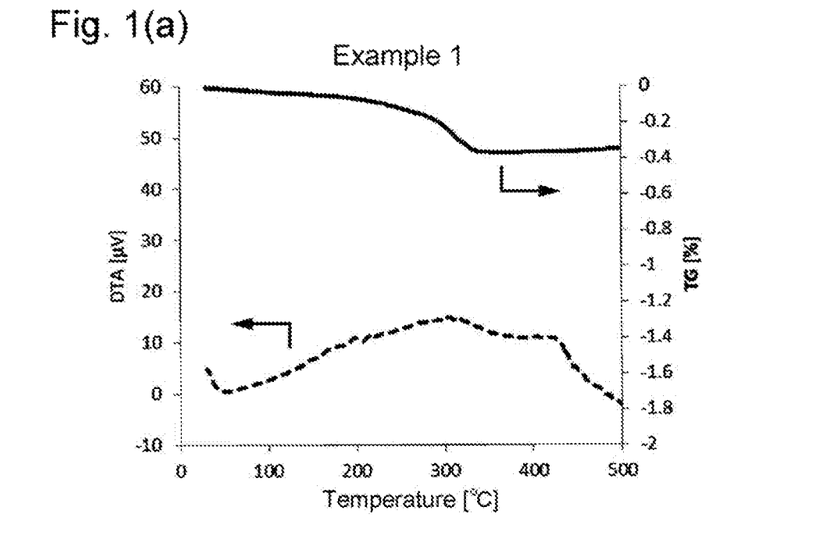
FIG. 1(a) and FIG. 1(b) are graphs showing the results of thermogravimetric differential thermal analysis (TG-DTA) on the surface-treated copper powders obtained in Examples 1 and 2, respectively.
Figure 1B:
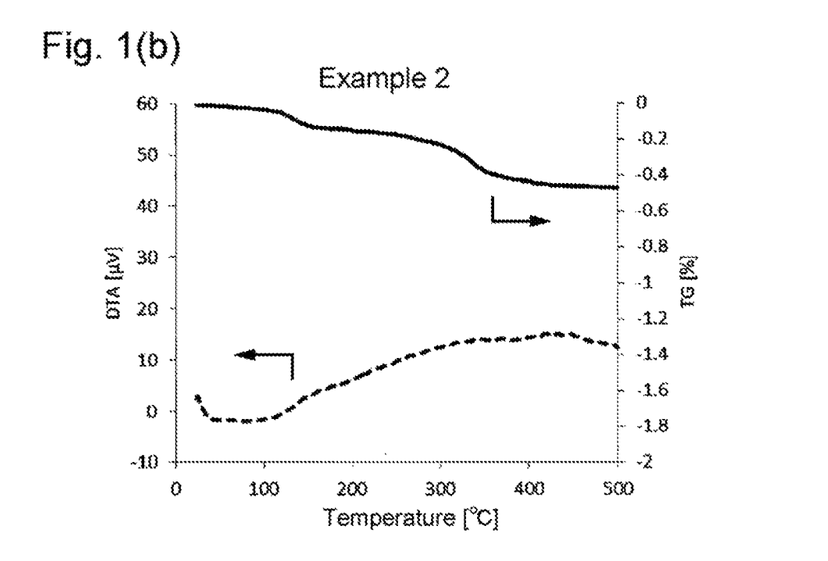
Figure 2A:
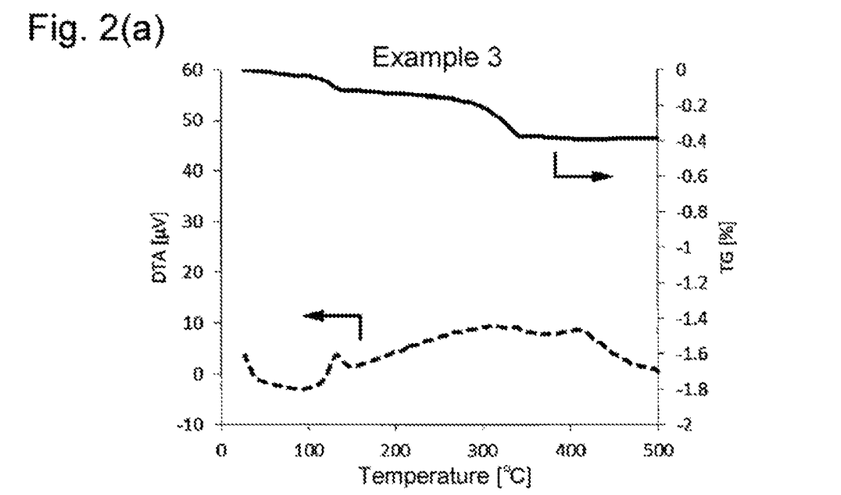
FIG. 2(a) and FIG. 2(b) are graphs showing the results of TG-DTA on the surface-treated copper powders obtained in Examples 3 and 4, respectively.
Figure 2B:
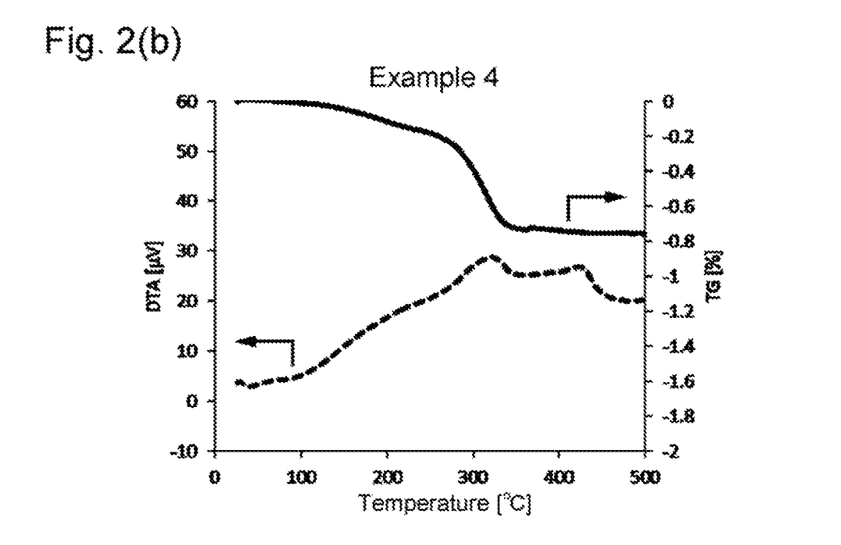
Figure 3A:
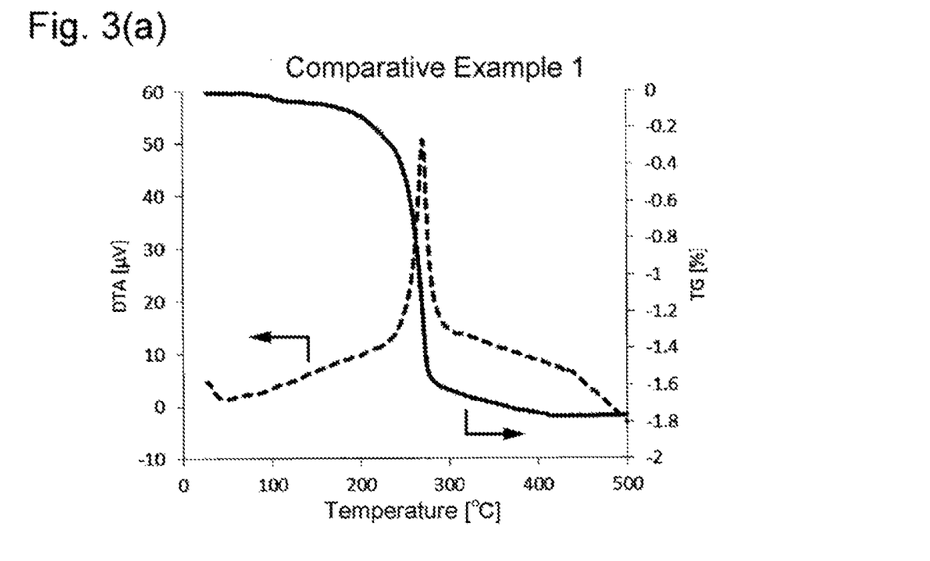
FIG. 3(a) and FIG. 3(b) are graphs showing the results of TG-DTA on the surface-treated copper powders obtained in Comparative Examples 1 and 2, respectively.
Figure 3B:
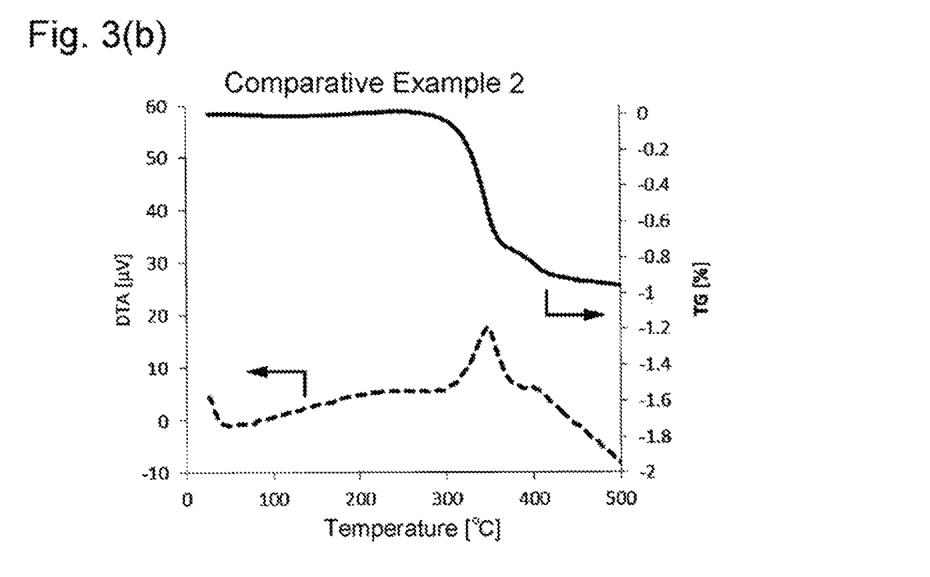
Figure 4A:
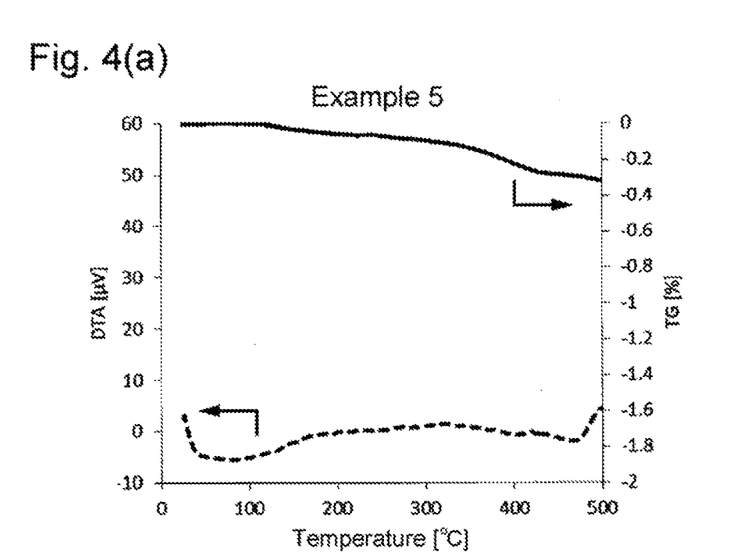
FIG. 4(a) and FIG. 4(b) are graphs showing the results of TG-DTA on the surface-treated copper powders obtained in Example 5 and Comparative Example 3, respectively.
Figure 4B:
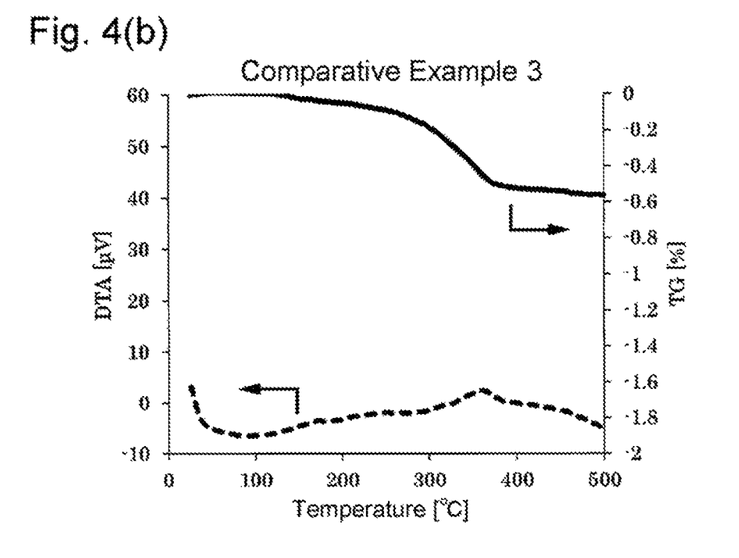

Evaluation:

The surface treated copper powders prepared in Examples and Comparative Examples were analyzed to determine the specific surface area SSA, average primary particle size D, carbon content PC, nitrogen content PN, and weight loss in thermogravimetry (from 25° C. to 500° C.) in accordance with the methods below. A heat resistance test was performed in accordance with the method below. The results obtained are shown in Table 1. The results of the TG-DTA on the surface treated copper powders prepared in Examples and Comparative Examples are shown in FIGS. 1 through 4, in which the solid lines and the broken lines indicate the results of TG and those of DTA, respectively.

Specific Surface Area SSA and Average Primary Particle Size D:

An SEM image was taken of the copper powder using a scanning electron microscope XL30SFEG from FEI Japan. The magnification was chosen between 5000 times and 30000 times according to the particle size so that at least 300 particles might be observed in a single field. The SEM image was analyzed on image analysis software Mac-View from Mountec Co., Ltd. to obtain the Heywood diameters of 300 or more particles per sample. The arithmetic average of the Heywood diameters was used to define the average primary particle size D.

Specific surface areas were calculated for the individual particles from their Heywood diameters according to the formula below, and the arithmetic average thereof was used to define the specific surface area SSA.

$$SSA=6/(\rho * d)$$

wherein SSA is a specific surface area (m²/g); $\rho$ is the density of copper (g/m³); and d is the Heywood diameter of each particle (m).

Carbon Content PC and Nitrogen Content PN:

The carbon content PC was determined using a carbon/sulfur analyzer for solid materials (EMIA-920V from Horiba, Ltd). The nitrogen content PN was determined using an oxygen/nitrogen/hydrogen analyzer (ONH836 from Leco Corp).

Weight Loss:

TG-DTA was carried out using TG-DTA2000SA from Bruker Corp. The sample was heated from 25° C. to 500° C. at a temperature increase rate of 20° C./min in a nitrogen atmosphere to determine the weight loss. The weight loss is a measure of the amount of the decomposition gas evolved on heating. The smaller the weight loss, the smaller the amount of the decomposition gas evolved.

Heat Resistance Test:

The surface-treated copper powder (before heating) was analyzed by XRD to obtain the ratio of the intensity of the (111) $Cu_2O$ (2θ=36°) ($I_{Cu2O}$) to the intensity of the (111) Cu (2θ=43°) ($I_{Cu}$), which will be referred to as pre-heating $I_{Cu2O}/I_{Cu}$. XRD was carried out using an X-ray diffractometer RINT-TITRIII from Rigaku Corp. The powder was then heated in the atmosphere for 1 hour and again analyzed by XRD to obtain post-heating $I_{Cu2O}/I_{Cu}$. The post-heating $I_{Cu2O}/I_{Cu}$ was expressed relatively with the pre-heating $I_{Cu2O}/I_{Cu}$ taken as 100%.

Heating was effected by placing 3 g of the surface-treated powder in a crucible and leaving it in a hot air dryer heated to a predetermined temperature.

The heating temperature was 100° C. and 110° C. in Examples 1 to 4 and Comparative Examples 1 and 2, and 125° C. and 135° C. in Example 5 and Comparative Example 3. The reason for varying the heating temperature is that oxidation resistance varies with particle size. The relative post-heating $I_{Cu2O}/I_{Cu}$ value is a measure of oxidation resistance of the copper powder. The smaller the value, the higher the oxidation resistance.

TABLE 1

| | Surface Treating Agent | SSA (m$^2$/g) | PC (%) | PN (%) | PC/SSA | PN/SSA | Average Primary Particle Size D (nm) | Weight Loss (%) | Post-Heating $I_{Cu2O}/I_{Cu}$ (relative to pre-heating $I_{Cu2O}/I_{Cu}$ (%)) | | | | |
|---|---|---|---|---|---|---|---|---|---|---|---|---|---|
| | | | | | | | | | before heating | 100° C. | 110° C. | 125° C. | 135° C. |
| Example 1 | dimethyl glyoxime | 5.83 | 0.10 | 0.042 | 0.017 | 0.0072 | 180 | 0.35 | 100 | 95 | 174 | | |
| Example 2 | ethylenediamine | 3.94 | 0.04 | 0.010 | 0.010 | 0.0025 | 234 | 0.47 | 100 | 118 | 131 | | |
| Example 3 | polyethyleneimine | 5.24 | 0.08 | 0.012 | 0.015 | 0.0023 | 177 | 0.39 | 100 | 102 | 126 | | |
| Example 4 | dimethyl glyoxime | 5.09 | 0.22 | 0.099 | 0.043 | 0.0195 | 171 | 0.75 | 100 | 101 | 165 | | |
| Example 5 | dimethyl glyoxime | 1.01 | 0.03 | 0.039 | 0.030 | 0.0386 | 820 | 0.32 | 100 | | | 92 | 172 |
| Compara. Example 1 | lauric acid | 5.26 | 0.63 | 0.018 | 0.120 | 0.0034 | 162 | 1.76 | 100 | 289 | 26254 | | |
| Compara. Example 2 | benzotriazole | 5.31 | 0.49 | 0.280 | 0.092 | 0.0527 | 178 | 0.95 | 100 | 157 | 279 | | |
| Compara. Example 3 | stearylamine | 0.86 | 0.17 | 0.038 | 0.198 | 0.0442 | 800 | 0.56 | 100 | | | 150 | 194 |

As is apparent from the results in Table 1, the surface-treated copper powders obtained in Examples show smaller weight losses than those of Comparative Examples, indicating reduction in gas generation. The surface-treated copper powders of Examples also prove less susceptible to oxidation than those of Comparative Examples.

As is clear from the results shown in FIGS. 1 through 4, the surface-treated powders of Examples show no distinct exothermic peaks when heated from 25° C. to 500° C., whereas those of Comparative Examples have a clear exothermic peak that is attributed to thermal decomposition of the organic compound used for the surface treatment.

Examples 6 to 8 and Comparative Example 4

An ink was prepared using each of the surface-treated copper powders obtained in Examples 1, 3, and 4 and Comparative Example 2, and a sintered body was formed using the ink. The joint strength of the sintered body was measured. Specific procedures were as follows.
(1) Preparation of Ink
An ink was prepared by mixing 5.6 g of the surface-treated copper powder, 4.4 g of CS-20 (a trade name of copper powder available from Mitsui Mining & Smelting), 0.7 g of triethanolamine, 0.08 g of diethanolamine, and 0.5 g of 3-glycidoxypropyltrimethoxysilane.
(2) Formation of Sintered Body
A 0.1 mg portion of the ink was applied to the center of a 5 mm-side square copper plate by dispenser printing, and a 3 mm-side square copper plate was placed thereon. The resultant was fired at 300° C. in a nitrogen atmosphere for 1 hour to form a sintered body joining the two copper plates.
(3) Determination of Joint Strength
The shear strength, which is a measure of the joint strength, of the sintered body was determined using a bond tester Condor Sigma from XYZTEC. A shear strength (MPa) is defined by breaking load (N)/joint area (mm$^2$). The results are shown in Table 2.
(4) Determination of Specific Resistance of Sintered Body
The specific resistance of a sintered body formed by firing the above prepared ink was determined. The ink was applied to a glass plate to form a coating film, and the coating film was fired at 300° C. for 1 hour to form a sintered body (conductive film). The specific resistance of the sintered body was determined using a four-probe resistivity meter Loresta MCP-HT600 from Mitsubishi Chemical Analytech Co., Ltd. The results are shown in Table 2.

TABLE 2

| | Surface-treated Copper Powder | Surface Treating Agent | Shear Strength (MPa) | Specific Resistance (μΩ · cm) |
|---|---|---|---|---|
| Example 6 | Example 1 | dimethyl glyoxime | 52 | 7 |
| Example 7 | Example 3 | polyethyleneimine | 47 | 16 |
| Example 8 | Example 4 | dimethyl glyoxime | 58 | 8 |
| Compara. Example 4 | Compara. Example 2 | benzotriazole | 5 | 200 |

As is apparent from the results in Table 2, the sintered body formed by using the copper powder obtained in each Example has high joint strength and low specific resistance.

INDUSTRIAL APPLICABILITY

The invention provides a copper powder having enhanced oxidation resistance and reduced gas evolution on firing and a conductive composition containing the same.

The invention claimed is:

1. A copper powder containing a carbon- and nitrogen-containing organic compound, having a ratio of carbon content PC (mass %) to specific surface area SSA (m$^2$/g), PC/SSA, of 0.010 to 0.08, and a ratio of nitrogen content PN (mass %) to specific surface area SSA (m$^2$/g), PN/SSA, of 0.002 to 0.04, and having a weight loss of 0.8 mass % or less when heated from 25° C. to 500° C. in a nitrogen atmosphere in thermogravimetry, said organic compound consisting of dimethyl glyoxime and covering the surface of a copper particle.

2. The copper powder according to claim 1, having a carbon content of 0.005 to 1 mass % and a nitrogen content of 0.001 to 0.5 mass %.

3. The copper powder according to claim 2, having an average primary particle size of 10 nm to 10 μm.

4. An electroconductive composition comprising the copper powder according to claim 2 and an organic solvent.

5. The copper powder according to claim 1, having an average primary particle size of 10 nm to 10 μm.

6. An electroconductive composition comprising the copper powder according to claim 1 and an organic solvent.

* * * * *